US011992197B2

(12) United States Patent
Johnsen et al.

(10) Patent No.: US 11,992,197 B2
(45) Date of Patent: May 28, 2024

(54) SET OF SAMPLING PARTS

(71) Applicant: AMBU A/S, Ballerup (DK)

(72) Inventors: Lasse Markworth Johnsen, Birkerød (DK); Jonas Hjortlund, Copenhagen S (DK); Martin Refslund Nielsen, Birkerød (DK)

(73) Assignee: AMBU A/S, Ballerup (DK)

( * ) Notice: Subject to any disclaimer, the term of this patent is extended or adjusted under 35 U.S.C. 154(b) by 0 days.

(21) Appl. No.: 18/210,523

(22) Filed: Jun. 15, 2023

(65) Prior Publication Data

US 2023/0320708 A1   Oct. 12, 2023

Related U.S. Application Data

(63) Continuation of application No. 16/610,340, filed as application No. PCT/DK2018/050086 on May 2, 2018, now Pat. No. 11,696,748.

(30) Foreign Application Priority Data

May 2, 2017   (DK) .......................... PA 2017 70293

(51) Int. Cl.
*A61B 10/04*   (2006.01)
*A61B 1/00*   (2006.01)
(Continued)

(52) U.S. Cl.
CPC .......... *A61B 10/04* (2013.01); *A61B 1/00066* (2013.01); *A61B 1/00128* (2013.01);
(Continued)

(58) Field of Classification Search
None
See application file for complete search history.

(56) References Cited

U.S. PATENT DOCUMENTS

| 4,643,197 A | 2/1987 | Greene et al. |
| 4,870,975 A | 10/1989 | Cronk et al. |

(Continued)

FOREIGN PATENT DOCUMENTS

| CN | 102271590 A | 12/2011 |
| CN | 103153199 A | 6/2013 |

(Continued)

OTHER PUBLICATIONS

Danish Search Report from corresponding Application No. PA 2017 70293, dated Jun. 20, 2017.

(Continued)

*Primary Examiner* — Benjamin S Melhus
(74) *Attorney, Agent, or Firm* — Faegre Drinker Biddle & Reath LLP

(57) ABSTRACT

A set of medical sampling parts for use with an endoscope, including: a sampling device; a sample container including a separator part located at a top of the sample container, a base located at a bottom of the sample container opposite of said top, and a container part at least partly enclosing a sample volume located at the bottom of the sample container, so that a container axis extends between said separator part and said base; and a connector for connecting the sampling device with the sample container, wherein the sample container can be detached from the sampling device by a translational movement along a detachment axis.

18 Claims, 10 Drawing Sheets

(51) Int. Cl.
*A61B 1/015* (2006.01)
*A61B 10/00* (2006.01)

(52) U.S. Cl.
CPC .......... *A61B 1/015* (2013.01); *A61B 10/0045* (2013.01); *A61B 10/0096* (2013.01)

(56) References Cited

U.S. PATENT DOCUMENTS

| | | |
|---|---|---|
| 4,909,782 A | 3/1990 | Semm et al. |
| 4,922,902 A | 5/1990 | Wuchinich et al. |
| 5,290,303 A | 3/1994 | Pingleton et al. |
| 5,334,183 A | 8/1994 | Wuchinich |
| 5,347,991 A | 9/1994 | Nakao et al. |
| 5,363,860 A | 11/1994 | Nakao et al. |
| 5,409,013 A | 4/1995 | Clement |
| 5,624,418 A | 4/1997 | Shepard |
| 6,110,127 A | 8/2000 | Suzuki |
| 6,190,330 B1 | 2/2001 | Harhen |
| 6,331,165 B1 | 12/2001 | Turturro et al. |
| 6,375,625 B1 | 4/2002 | French et al. |
| 6,632,182 B1 | 10/2003 | Treat |
| 6,840,909 B2 | 1/2005 | Gatto |
| 6,852,108 B2 | 2/2005 | Barry et al. |
| 7,172,579 B2 | 2/2007 | Barzell et al. |
| 7,708,938 B2 | 5/2010 | Mariotti et al. |
| 7,806,835 B2 | 10/2010 | Hibner et al. |
| 8,382,660 B2 | 2/2013 | Okada |
| 8,460,182 B2 | 6/2013 | Ouyang et al. |
| 8,974,399 B2 | 3/2015 | Teixeira et al. |
| 9,204,868 B2 | 12/2015 | Furlong et al. |
| 9,332,969 B2 | 5/2016 | Han et al. |
| 9,408,593 B2 | 8/2016 | Furlong et al. |
| 9,421,001 B2 | 8/2016 | Speeg et al. |
| 9,486,185 B2 | 11/2016 | Hibner |
| 9,486,186 B2 | 11/2016 | Fiebig et al. |
| 9,498,193 B2 | 11/2016 | Smith et al. |
| 9,538,994 B2 | 1/2017 | Hibner et al. |
| 9,545,244 B2 | 1/2017 | Parihar et al. |
| 9,603,587 B2 | 3/2017 | Fiebig et al. |
| 9,737,285 B2 | 8/2017 | Fiebig et al. |
| 11,696,748 B2 | 7/2023 | Johnsen et al. |
| 2004/0068291 A1 | 4/2004 | Suzuki |
| 2007/0088199 A1 | 4/2007 | Ito et al. |
| 2007/0179341 A1 | 8/2007 | Okada |
| 2007/0191731 A1 | 8/2007 | Kaye et al. |
| 2007/0213632 A1 | 9/2007 | Okazaki et al. |
| 2008/0082021 A1 | 4/2008 | Ichikawa et al. |
| 2008/0163669 A1 | 7/2008 | Gregory et al. |
| 2008/0183037 A1 | 7/2008 | Ichikawa et al. |
| 2009/0234192 A1 | 9/2009 | Okada |
| 2010/0174210 A1 | 7/2010 | Han et al. |
| 2012/0095369 A1 | 4/2012 | Teixeira et al. |
| 2013/0123663 A1 | 5/2013 | Hibner et al. |
| 2013/0144186 A1 | 6/2013 | Furlong |
| 2014/0088460 A1 | 3/2014 | Teixeira et al. |
| 2014/0378864 A1 | 12/2014 | Hibner |
| 2015/0209491 A1 | 7/2015 | Cushner et al. |
| 2016/0256139 A1 | 9/2016 | Hadley et al. |
| 2019/0038195 A1 | 2/2019 | Peterson et al. |
| 2019/0054217 A1 | 2/2019 | Axon |
| 2020/0121304 A1 | 4/2020 | Johnsen et al. |
| 2020/0188921 A1 | 6/2020 | Goodman |
| 2022/0338846 A1 | 10/2022 | Johnsen et al. |

FOREIGN PATENT DOCUMENTS

| | | |
|---|---|---|
| EP | 1813184 A1 | 8/2007 |
| EP | 1908391 A1 | 4/2008 |
| EP | 2100550 A1 | 9/2009 |
| WO | 99/08731 A1 | 2/1999 |
| WO | 2006/039646 A2 | 4/2006 |
| WO | 2008/144515 A1 | 11/2008 |
| WO | 2012/051545 A2 | 4/2012 |
| WO | 2014/028366 A1 | 2/2014 |
| WO | 2015/031217 A1 | 3/2015 |
| WO | 2016/196536 A1 | 12/2016 |
| WO | 2017/075415 A1 | 5/2017 |
| WO | 2017/087411 A1 | 5/2017 |

OTHER PUBLICATIONS

Examination Report issued in EP18722887.9, dated Aug. 19, 2022, 6 pages.
Examination Report issued in EP18722888.7, dated Jan. 13, 2021, 5 pages.
First Office Action issued in Chinese Patent Application No. 201880028621.7, dated Jul. 30, 2021.
First Office Action issued in CN201880028621.7, dated Jul. 30, 2021, with informal translation.
Global dossier translation of notification of grant from CN application No. 201880028621.7, mailed Feb. 9, 2022, 2 pgs.
Global dossier translation of office action from CN application No. 201880025464.4, mailed Dec. 28, 2021, 6 pgs.
Global dossier translation of office action from CN application No. 201880028621.7, mailed Jul. 30, 2021, 7 pgs.
International Search Report and Written Opinion from corresponding Application No. PCT/DK2018/050086, dated Aug. 22, 2018.
International Search Report and Written Opinion from corresponding Application No. PCT/DK2018/050087, dated Jul. 3, 2018.
International Search Report and Written Opinion received for PCT Patent Application No. PCT/DK2018/050087, mailed on Jul. 3, 2018, 11 pages.
Office Action received for Chinese Patent Application No. 201880025464, mailed on Jun. 27, 2022, 7 pages (4 pages of English Translation and 3 pages of Original Document).
Office Action received for Chinese Patent Application No. 201880025464, mailed on Dec. 28, 2021, 12 pages (6 pages of English Translation and 6 pages of Original Document).
Search report from EP application No. 18722887.9, mailed Jan. 12, 2021, 5 pgs.

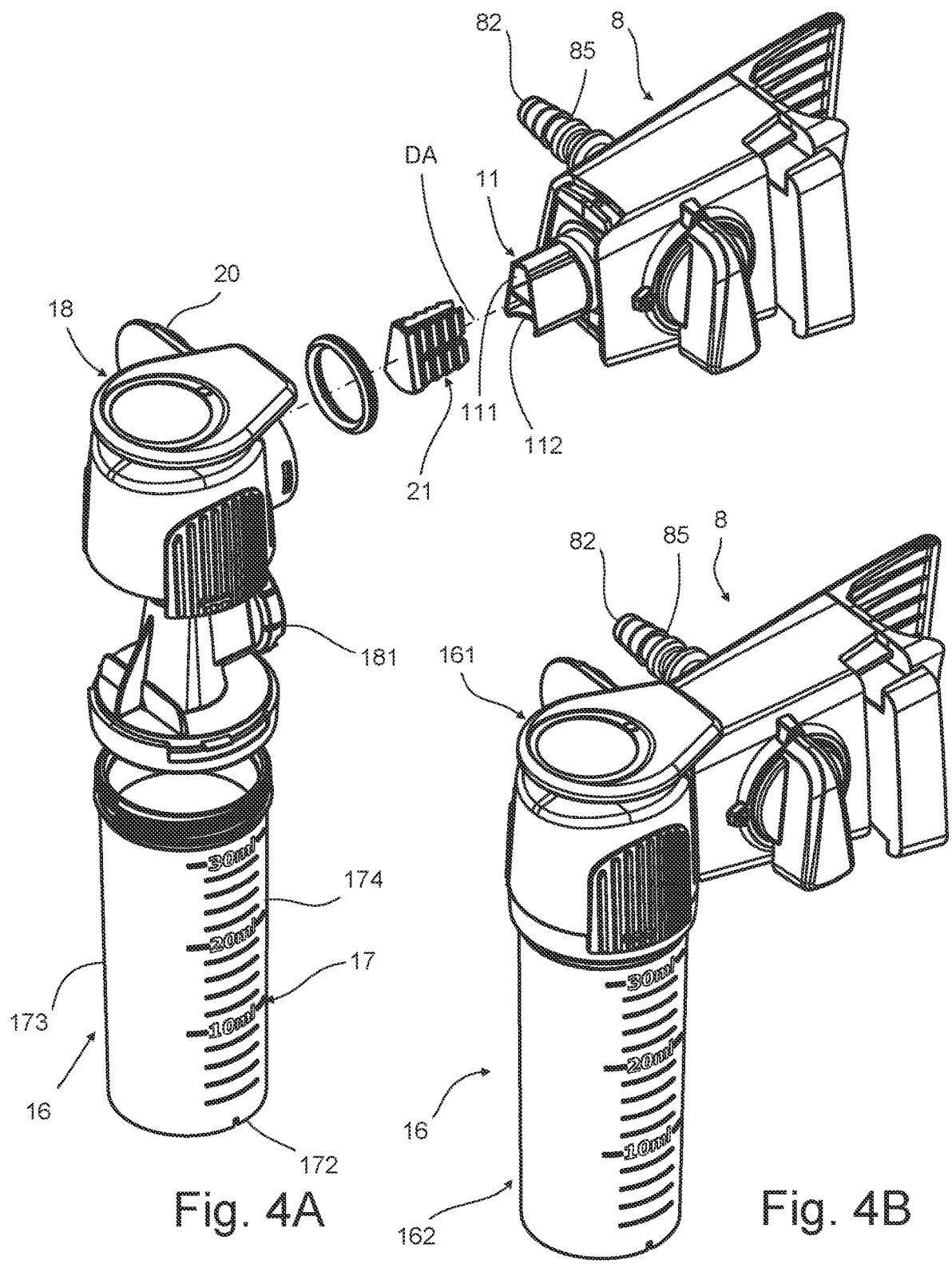

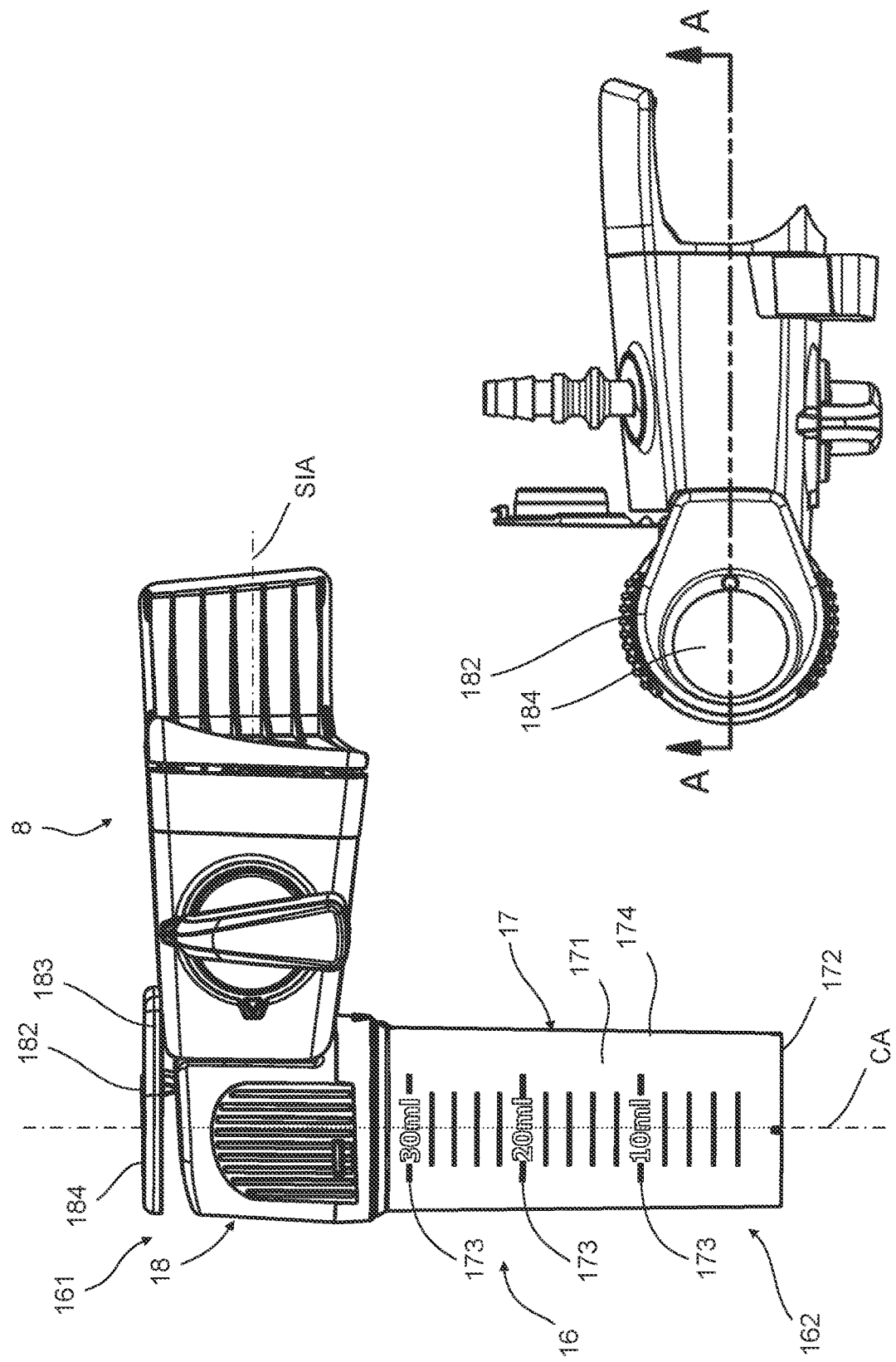

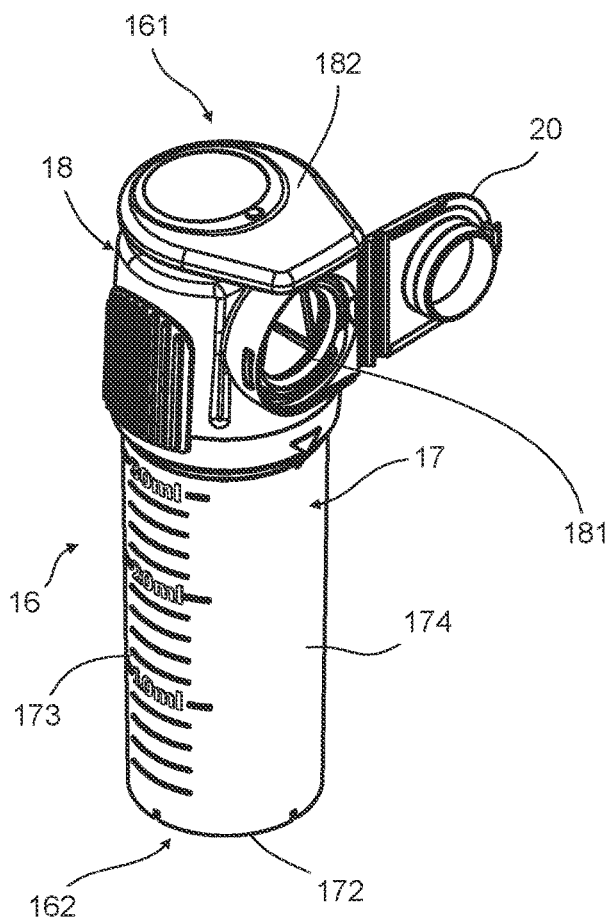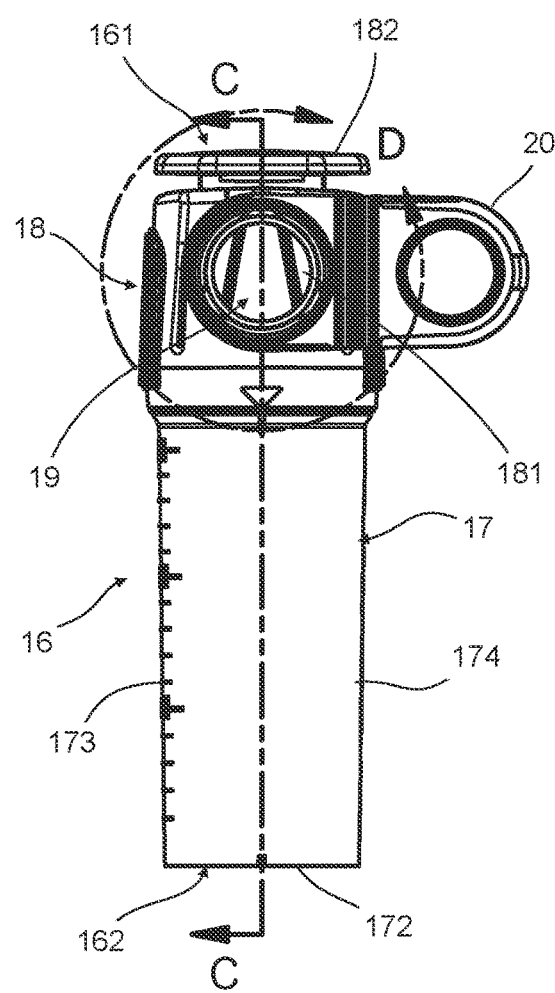
Fig. 8A
Fig. 8B

SET OF SAMPLING PARTS

CROSS-REFERENCE TO RELATED APPLICATIONS

This application is a continuation of U.S. patent application Ser. No. 16/610,340, filed Nov. 1, 2019, which is a National Stage application filed under 35 U.S.C. § 371 of International Application No. PCT/DK2018/050086, filed on May 2, 2018, which claims the benefit of Denmark Patent Application No. PA 2017 70293, filed on May 2, 2017. Said applications are incorporated herein by reference in their entirety.

TECHNICAL FIELD

The present invention relates to a set of medical sampling parts for use with an endoscope or a catheter for flushing of a body cavity and/or for sampling of bodily fluids and/or bodily tissue, the endoscope or catheter having a suction channel and a suction connector in communication with said suction channel.

BACKGROUND

Endoscopes are well known devices for visually inspecting parts of a body of a human or animal, which may be difficult to access, such as human body cavities. Typically, an endoscope comprises an elongated insertion tube with a handle at a proximal end as seen from an operator, and visual inspections means, such as a built-in camera, at a distal end of the elongated insertion tube. This definition of the terms distal and proximal, i.e. proximal being the end closest to the operator and distal being the end remote from the operator, as used herein for endoscopes in general, is adhered to in the present specification. Electrical wiring for the camera and other electronics such as LED lighting typically runs along an inside of the elongated insertion tube from the handle to the tip at the distal end. Instead of using cameras, endoscopes may also be fibre-optic, in which case the optical fibres typically run along an inside of the elongated insertion tube. A working or suction channel may run along the inside of the insertion tube from the handle to the tip, allowing liquid to be removed from the body cavity or allowing for insertion of surgical instruments or the like into the body cavity. The suction channel may be connected to a suction connector, typically positioned at a handle at the proximal end of the insertion tube.

An endoscope as mentioned above are, inter alia, used in procedures such as bronchial lavage (BL), bronchial wash (BW) or bronchoalveolar lavage (BAL), which are commonly used procedures for obtaining samples of organic material from a lung segment of a patient. These may be carried out by flushing a lung segment with sterile water, usually a sterile aqueous saline solution, and then sucking the water into a sample container. More specifically, the distal end of the insertion tube of an endoscope is advanced to the location in the lung where the sample is to be taken. In bronchoalveolar lavage, the distal end is then pressed into firm engagement against the interior of the lung to help securing the position in a process commonly referred to as wedging.

Via the suction channel of the endoscope, fluid, such as sterile water, e.g. a 0.9% saline solution, or isotonic saline, is instilled into the lung at the sample location and as much as possible extracted again, now containing organic material in the form of bodily fluids and/or tissue, and thus constituting a medical sample. Typically, this is done by attaching a filled syringe of a volume between 20 ml and 60 ml, e.g. 50 ml to the suction channel of the endoscope, via a communication port in endoscope handle. The syringe is then used for each instillation as well as the subsequent extraction. This process is normally repeated several times in a row with new syringes, e.g. three to four, the samples being suitable for various purposes, depending which number of sample in the sequence they are, because the composition of the organic material varies. If the syringe is used for extraction, the sample would be transferred to a sample container suitable for securing biological material. Upon extraction, the sample containers are, therefore, normally labelled accordingly.

As an alternative to extraction using the syringe, the extraction may be performed in-line using an external suction and a Lukens trap, e.g. as disclosed in U.S. Pat. No. 4,643,197.

Using a Lukens trap attached to the endoscope in the manner disclosed in U.S. Pat. No. 4,643,197, i.e. interposed in the flexible suction line leading from the endoscope to the vacuum source or suction source (the two terms are used synonymously in the present specification), may involve several disadvantages when carrying out the procedure. One such disadvantage may be that the operator has only little sense of and attention to the orientation of the trap being suspended on the line since the operator's attention may be focused on other parts of the procedure, e.g. the delicate parts of the procedure within the patient. It, therefore, may happen that the Lukens trap inadvertently ends up in an orientation where the sample is lost because it gets sucked out of the trap by the suction source. Another disadvantage is that there is a lot of work involved in connecting and disconnecting tubes as well as other parts, e.g. if the operator needs to change between obtaining a sample and suction in order to clean without sampling. Another disadvantage may be that a liquid surface of the sample in the Lukens trap may comprise surface froth caused by agitation by the sampling gas, this is disadvantageous when attempting to measure the volume of the obtained sample since it is difficult to visually assess the level of the sample.

U.S. Pat. No. 6,375,625 discloses an in-line specimen trap with a cap coupled to a sample container. A rotatable member in the cap comprises through-going openings and may be rotated to provide fluid communication between inlets and outlets.

SUMMARY OF DISCLOSED EMBODIMENTS

On this background, it may be seen as an object of the present invention to provide a set of medical sampling parts, which may be cheaper or easier in manufacture thereof, may provide improved sealing properties thereof, may provide easier or simpler operation thereof, may improve sample-taking, and/or may reduce a risk of losing the sample.

One or more of these objects may be met by the present invention as described in the following.

A first aspect of the invention relates to a set of medical sampling parts for use with an endoscope or catheter for flushing of a body cavity and/or for sampling of bodily fluids and/or bodily tissue, the endoscope or catheter having a suction channel and a suction connector in fluid connection with said suction channel, the set of medical sampling parts comprising a sampling device including a suction inlet for connection to a suction connector of the endoscope or catheter, and a suction outlet for connection to a vacuum source; a sample container including a separator part located at a top of the sample container, a base located at a bottom of the sample container opposite of said top, and a container part at least partly enclosing a sample volume located at the bottom of the sample container, so that a container axis extends between said separator part and said base, said base potentially allowing stable support of the sample container on a level surface, so that the container axis is substantially perpendicular or perpendicular to a surface level of a liquid sample when a liquid sample is contained in the sample volume and the base rests on a level support surface; and a connector for connecting the sampling device with the sample container, wherein the set of medical sampling parts has an assembled state, in which the sampling device and the sample container are attached to each other by means of said connector, and a detached state, in which the sample container is detached from the sampling device; wherein, in said assembled state, a first fluid connection is established between said sample container and said suction inlet, and a second fluid connection is established between said sample container and suction outlet, so that, when a sampling fluid comprising liquid and gas enters the sample container via the first fluid connection, the sampling fluid can be separated in the separator part of the sample container by discharging liquid of the sampling fluid into said sample volume and by discharging the gas of the sampling fluid via said second fluid connection; and wherein the sample container in said assembled state can be detached from the sampling device by a translational movement of the sample container along a detachment axis to bring the set of medical sampling parts to said detached state, whereby a smallest angle between said container axis and said detachment axis is equal to or greater than 45 degrees, potentially equal to or greater than 50, 55, 60, 65, 70, 75, 80, or 85 degrees.

When performing procedures such as bronchial lavage (BL), bronchial wash (BW) or bronchoalveolar lavage (BAL), which are commonly used procedures for obtaining samples of organic material from a lung segment of a patient, the set of medical sampling parts are typically held at a position above the patient so that the insertion tube extends along a longitudinal direction mainly being vertical. By providing a set of medical sampling parts in this way displacements, such as jerks when detaching or attaching the sample container, will mainly be in the horizontal direction, i.e. a transverse direction to the endoscope, and therefore be less likely to cause any displacement of the endoscope in the vertical direction, i.e. longitudinal direction. Such longitudinal displacement is undesired as the displacement could cause the tip of the endoscope to move within the patient, which could result in loss of the wedge position and thereby extend the time to complete the procedure. Such longitudinal displacements are also undesired since the sample contained in the sample container may inadvertently be displaced closer to the second fluid connection risking losing some of the sample when detaching the sample container.

Furthermore, the fluid connections between the sample container and the remaining set of medical sampling parts may be disconnected in a single movement, this may provide a simpler operation of the set of medical sampling parts, especially if multiple samples are to be taken from the same patient.

By providing a set of medical sampling parts with a simpler operation, the number of caregivers required to perform the above procedures may be reduced, potentially so that only one caregiver is required to perform the above procedures.

The sampling fluid may further comprise organic material, such as bacteria, vira, particles, and/or tissue, potentially when performing the above procedures.

The smallest angle is measured in a plane, which comprises the detachment axis and at least a projection of the container axis. Preferably the detachment axis intersects the container axis, so that the smallest angle may be measured in a plane parallel to the detachment axis and the container axis. The smallest angle is the smaller of the two angles between the container axis and the detachment axis. The smallest angle may be defined by the smaller of two angles found by rotating the detachment axis clockwise and counter-clockwise in a common plane about the intersection of the container axis and detachment axis until the detachment axis coincide with the container axis.

Whether a base of a sample container provides stable support may be tested by placing the base of the sample container in the detached state on a non-adhering surface which is inclined with +/−10°, preferably 20°, more preferably 30°, relative to level in any direction and test if the sample container roll or tip.

The set of medical sampling parts may further comprise a cap part located at the top of the sample container, wherein the container axis extends between the oppositely located base and cap part of the sample container. The cap part and the container part may fully enclose the sample volume.

Additionally or alternatively, the cap part may be removable from the remaining parts of the sample container. Additionally or alternatively, the cap part may comprise the separator part or reversely. Additionally or alternatively, the cap part may accommodate the separator part or reversely. The container part may have the form of a test tube or a cylinder closed at one end, which may potentially be closed with the cap.

The container axis may be vertical if the base rests on a level surface. Additionally or alternatively, the container axis may be vertical if the sample container rests on a level surface, potentially only supported by the base.

The container axis may be a centre axis, potentially a symmetry axis, potentially a rotational symmetry axis of the container part. The sample container may be cylindrical and the container axis may be a centre axis of the cylindrical sample container, potentially a centre rotational symmetry axis. The sample container may be box-shaped and the container axis may be a centre axis of the box shaped sample container.

The container part may further comprise at least one liquid level mark allowing visual measurement of the volume of liquid contained in the sample volume of the container part, wherein the liquid level mark extends in a plane perpendicular to the container axis. The at least one liquid level mark may be adapted to extend in parallel to a liquid level of a liquid sample in the sample volume of the sample container when the sample container, specifically said base thereof, rests on a level surface.

The sample container in the assembled state may be fixed at least radially to the sampling device in relation to the detachment axis. Additionally or alternatively, the sample container in the assembled state may be at least longitudinally fixed to the sampling device, potentially by a locking device. The sample container in the assembled state may be rigidly fixed to the sampling device in relation to the detachment axis.

An angle between a centre axis of said suction inlet and said container axis may be fixed in said assembled state.

The sampling device and the sample container may be attached rigidly to each other in said assembled state. As mentioned above there is always a risk that the operator may inadvertently orientate the sample container so that the collected sample is lost to the suction source through the second fluid connection. By attaching the sample container rigidly to the sampling device, the sample container is adapted to extend in a well-defined manner from the endoscope, because of the rigid cooperation between set of medical sampling parts. Accordingly, the sampling device and the sample container follows the movements of the endoscope, or more specifically the handle of the endoscope. Since the operator is used to gripping the handle of the endoscope and familiar with the orientation thereof, the likelihood that the endoscope ends up in an orientation where the sample is lost, is reduced.

The sampling device may be made of or may comprise a rigid material, so that, when in said assembled state and the sampling device is connected to the endoscope or catheter, the sampling device establishes a rigid connection between the sample container and the endoscope or catheter.

In this disclosure, a rigid feature may alternatively be defined as the material forming the feature have a Young's modulus of at least 1 GPa, preferably at least 5 GPa, more preferably at least 10 GPa, most preferably at least 20 GPa.

The first and/or second fluid connections may be rigid connections in the assembled state.

The sample container in the detached state may be able to be attached, potentially translationally attached, to the sampling device along an attachment axis, wherein a smallest angle between the container axis and the attachment axis may be equal to or greater than 45 degrees, potentially equal to or greater than 50, 55, 60, 65, 70, 75, 80, or 85 degrees, the detachment axis and the attachment axis preferably being parallel, more preferably being coinciding.

The sampling device may comprise the connector, the connector potentially being an integral part of the sampling device.

The connector may be a protrusion, potentially a spout and/or potentially extending along the detachment axis in the assembled state.

The connector of the set of medical sampling parts may comprise: a sampling inlet forming part of the first fluid connection and being able to eject sampling fluid into the sample container along an inlet direction; and a sampling outlet forming part of the second fluid connection and being able to discharge sampling gas of the sampling fluid along an outlet direction. Additionally or alternatively, an angle between an centre axis of sampling inlet and the container axis may be fixed. The sampling outlet may be located closer to the top of the sample container relative to the sampling inlet in the assembled state. Additionally or alternatively, the inlet direction and outlet direction may extend in parallel. Alternatively or additionally, the inlet direction and outlet direction may extend oppositely. Alternatively or additionally, the inlet direction and outlet direction may extend in parallel with the container axis or the detachment axis. The sampling inlet may have a first hydraulic diameter and the sampling outlet may have a second hydraulic diameter, the first hydraulic diameter may be greater than the second hydraulic diameter, potentially the first hydraulic diameter may be at least 1.1 times, 1.2 times, 1.3 times, 1.4 times, 1.5 times, 1.6 times, 1.7 times, 1.8 times, 1.9 times, 2 times, 3 times, 4 times, 5 times, 6 times, 7 times, 8 times, 9 times, or 10 times greater than the second hydraulic diameter.

The sample container may comprise a side wall connecting said top and base, wherein the detachment axis may extend through the side wall in the assembled state, the side wall potentially extending in parallel with the container axis.

The set of medical sampling parts, potentially the sample container, may further comprise a locking device configured to lock the sample container to the sampling device in the assembled state, potentially by snap locking. The locking device of the sample container may comprise a snap lever able to lock the sample container to the sampling device in the assembled state. The locking device may be configured to be operated with one hand, potentially when gripping the sample container, potentially by a thumb.

The set of medical sampling parts, potentially the connector, may comprise a flow path extension device, potentially being a separate part, wherein a centre flow path of gas of the sampling fluid flowing between the sampling inlet and the sampling outlet is extended or prolonged compared to if the flow path extension device was not present. This may provide the advantage that the amount of liquid discharged into the sample container part is increased, since the distance travelled by the sampling fluid, inside the separator part is increased and thus allowing more of the sampling liquid to be discharged. Additionally or alternatively, a hydraulic diameter of a portion of the first fluid connection and/or of the second fluid connection may be reduced compared to if the flow path extension device was not present. Additionally or alternatively, the flow path extension device in the assembled state reduces a hydraulic diameter of a portion of the first fluid connection and/or of the second fluid connection relative to if the flow path extension device is not present in the assembled state. Additionally or alternatively, the flow path extension device can reduce a hydraulic diameter of a portion of the first fluid connection and/or of the second fluid connection in the assembled state. The flow path extension device may be in the form of a plug comprising a head and a body, the flow path extension device being inserted into the connector in said assembled state, potentially being inserted into a sampling inlet and/or a sampling outlet of the connector in said assembled state. The body may comprise a duct forming part of said first or said second fluid connection in said assembled state, so as to reduce the hydraulic diameter of at least a portion of the first and/or the second fluid connection compared to if the flow path extension device was not present. Additionally or alternatively, the body may comprise a first duct and a second duct, wherein the first duct forms a part of said first fluid connection in the assembled state, and the second duct forms a part of said second fluid connection in the assembled state, so as to reduce the hydraulic diameter of at least a portion of the first and the second fluid connection compared to if the flow path extension device was not present. Said portion of the first and second fluid connection may be accommodated in the connector. The flow path extension device may be at least partly made of a sealing material, potentially a rubber material, so that the flow path extension device seals the connector, so as to urge the sampling fluid to enter the sample container along the first fluid connection, and potentially to leave the sample container along the second fluid connection. This may provide the advantage that sampling fluid is prevented from leaking from the first fluid connection, and/or that sampling fluid is urged along the first fluid connection, so as to provide a good separation of the sampling fluid. The body of the flow path extension device may comprise a barb adapted for resisting removal of the flow path extension device from the connector. This may provide the advantage that accidental removal may be prevented and/or that tightness may be increased. The flow path extension device may be an elongated plug extending along a longitudinal direction, potentially along the detachment axis in the assembled state.

The sampling device may further comprise a sampling valve having a bypass mode and a sampling mode, wherein, when the sampling valve is in the sampling mode, sampling fluid may be allowed to flow through the sample container via the first and second fluid connection, and wherein, when the sampling valve is in the bypass mode, sampling fluid may be allowed to flow via a third, different fluid connection between the suction inlet and suction outlet of the sampling device. Additionally or alternatively, the third fluid connection is preferably different from the first and second fluid connection. Additionally or alternatively, the sample container, potentially the sample volume of the sample container, is not a part of the third fluid connection.

The connector may be adapted to penetrate at least one seal of the sample container. This may reduce the risk of infection by automatically sealing the sample container when detached from the sampling device. Additionally or alternatively, the connector may, upon attaching the sample container to the sampling device, penetrate at least one seal of the insertion hole of the sample container, so as to establish the first and second fluid connections.

The set of medical sampling parts may further comprise an endoscope or catheter including a suction channel and a suction connector in fluid connection with said suction channel, wherein the set of medical sampling parts includes an operating state in which the sample container, the sampling device, and the connector is in the assembled state and the suction connector is in fluid connection with the suction inlet of the sampling device, wherein the first fluid connection extends through said suction channel via the suction connector of the endoscope or catheter in the assembled state so that flushing of a body cavity can be performed and/or a sample of bodily fluids and/or bodily tissue can be conveyed to the sample container. The endoscope further comprises a handle with a bottom, wherein at least the top of the sample container, potentially at least the bottom of the sample container, is located at a greater height than the bottom of the handle along the container axis. The height direction may alternatively be defined as a longitudinal length direction of the handle of the endoscope. This may allow an operator to quickly assess the volume of the obtained sample, since the sample container is easily visually inspected. The bottom of the handle may be located at a little finger of a gripping hand if gripping the handle. The endoscope may further comprise an insertion tube having a distal end configured for insertion into a body cavity, wherein a proximal end of the insertion tube is connected to the bottom of the handle.

A second aspect of the invention relates to a sample container for connecting to a connector of a sampling device, comprising: a container part at least partly enclosing a sample volume located at a bottom of the sample container; a cap part located at a top of the sample container and including an insertion hole able to receive and attach said connector and able to establish a fluid connection between said sampling device and the sample volume of the container part, the insertion hole extending along a detachment axis; a base for supporting the sample container, the base being located oppositely from the cap part at the bottom of the sample container; and a container axis extending between the cap part and the base of the sample container, wherein the insertion hole has a cross-sectional shape, which is perpendicular to said detachment axis, and which extends substantially uniformly for at least 3 mm, the cross-sectional shape being a substantially convex keyhole shape, so that when said connector is inserted into the insertion hole along said detachment axis, if the connector has an exterior shape corresponding to the cross-sectional shape of the insertion hole, said connector can be attached, potentially at least radially fixed, in said insertion hole in relation to said detachment axis, and the sample container can be attached and detached from the sampling device by a translational movement of the sample container along said detachment axis, wherein a smallest angle between said container axis and said detachment axis is equal to or greater than 45 degrees, potentially equal to or greater than 50, 55, 60, 65, 70, 75, 80, or 85 degrees.

This may provide the advantage that the sample container can be detached along a transverse direction to an endoscope, which is typically horizontal. The operator is therefore less likely to cause any displacement of the endoscope in the vertical direction. A further advantage may be that the sample container is only allowed to be attached in substantially one orientation, typically a substantially vertical orientation, this may also ensure that the fluid connections are established as intended so that the separation of sampling fluid can occur.

Additionally or alternatively, the cross-sectional shape may be convexly keyhole shaped so that attaching the sample container to the sampling device can only happen with one orientation of the sample container.

Additionally or alternatively, the cross-sectional shape of the insertion hole may extend substantially uniformly along said detachment axis for at least 3 mm, potentially for at least 4 mm, 5 mm, 6 mm, 7 mm, 8 mm, 9 mm, 10 mm, 12 mm, 15 mm. By increasing the uniform extension of the cross-sectional shape of the insertion hole, the detaching movement will increasingly be urged along a centre axis of the insertion hole, further reducing the risk of accidental tip displacements of the endoscope.

Additionally or alternatively, the insertion hole of the sample container may comprise a penetrable seal adapted to allow a connector of a sampling device to pass through and to seal the insertion hole upon detaching a connector of a sampling device.

Additionally or alternatively, the cross-sectional shape of the insertion hole may be a quadrilateral with a first pair of opposite sides having equal length and a second, different pair of opposite sides having unequal length. The first pair of sides may be reflection symmetric, potentially in a plane defined by the detachment axis and/or container axis. The length of each side of the first pair of sides of the quadrilateral may be between 11.0-12.8 mm, preferably 11.3-12.5 mm, more preferably 11.6-12.2 mm. The distance between the end points of the top side of the second pair of sides, L1, may be less than 75%, 70%, 65%, 60%, 55%, or 53% of the distance between the end points of the bottom side of the second pair of sides, L2. The distance between the end points of the top side of the second pair of sides, L1, may be between 4.0-5.8 mm, preferably 4.3-5.5 mm, more preferably 4.6-5.2 mm, and/or the distance between the end points of the bottom side of the second pair of sides, L2, may be between 8.3-10.1 mm, preferably 8.6-9.8 mm, more preferably 8.9-9.5 mm.

Both sides of the second pair of sides of the quadrilateral may be curved, potentially convexly or outwardly curved, and potentially having equal curvature, and preferably having a common centre of curvature. The curvature of each of the second pair of sides of the quadrilateral may have a diameter, D, between 13.0-15.7 mm, preferably 13.5-15.2 mm, more preferably 14.0-14.7 mm.

The insertion hole may extend longitudinally along an insertion axis so that the smallest angle between the insertion axis and the container axis is equal to or greater than 45 degrees, potentially equal to or greater than 50, 55, 60, 65, 70, 75, 80, or 85 degrees. The insertion axis may be parallel to the detachment axis, potentially be the same as the detachment axis.

The sample container may further comprise a sealing lid having a closed state, in which the sealing lid sealingly close the insertion hole, and potentially an open state. The sealing lid may allow a user to close the sealing lid with one hand. The sealing lid may be hingedly connected to the sample container, potentially the cap part of the sample container.

The sample container may further comprise a locking device adapted to lock the sample container to a sampling device, potentially upon connection and/or by snap locking. The sealing lid may further comprise a locking device able to lock the sealing lid in the closed state. The locking device may allow a user to disengage, and potentially engage, the locking device with one hand.

The cap part and the container part may be able to be detached from each other.

The distance between the inlet of the insertion hole into the sample container and the bottom of the sample volume may be at least 50, 55, 60, 65, 70, or 75 mm. This may prevent sample frothing when sampling easing the visual volume measurement of the sample.

The sample container of the set of medical sampling parts of the first aspect may be according to the second aspect.

A third aspect of the invention relates to a method for assembly of medical sampling parts and an endoscope or catheter, comprising the steps of: providing a set of medical sampling parts according to the first aspect of the invention; connecting the sampling device with a suction connector of the endoscope or catheter; and attaching the sample container with the sampling device, thereby bringing the set of medical sampling parts to the operating state.

The method may further comprise the step of extracting a sample, potentially from a body cavity, via the endoscope to the sample container, potentially by a bronchoalveolar lavage, BAL, procedure.

A fourth aspect of the invention relates to a method for detaching a sample container from a sampling device, comprising the steps of: providing a set of medical sampling parts according to the first aspect of the invention in said assembled state; detaching the sample container from the sampling device by a movement of the sample container along said detachment axis; potentially closing a lid of the sample container to seal the sample contained in the sample container; and potentially attaching another sample container to the sampling device along the detachment axis.

A fifth aspect of the invention relates to the use of a sample container according to the second aspect of the invention for receiving a sample from a sampling device.

A sixth aspect of the invention relates to a sampling device for the use with an endoscope having a suction channel and a suction connector in communication with said suction channel, said sampling device being adapted for connection to the suction connector and said sampling device being adapted for connection to a vacuum source, wherein said sampling device is adapted for forming a rigid connection with said endoscope when connected to the suction connector thereof.

In some embodiments, the sampling device comprises a socket defining an insertion direction adapted to receive the suction connector of the endoscope in said insertion direction for forming said rigid connection, and the sampling device is furthermore adapted to engage the endoscope in a manner preventing rotation around the suction connector.

In some embodiments, the sampling device comprises a male connector defining an insertion direction adapted to engage a suction connector socket of the endoscope in said insertion direction for forming said rigid connection, and the sampling device is furthermore adapted to engage the endoscope in a manner preventing rotation around the suction connector.

In some embodiments, the sampling device comprises a valve for diverting the suction through the sampling device through a sample container.

In some embodiments, the sampling comprises a valve actuator for activating the suction through the sampling device.

In some embodiments, the sampling device comprises a sample container connector adapted for connecting a sample container.

In some embodiments, the sample container connector extends in a direction parallel to or coincident with said insertion direction.

In some embodiments, the sample container connector is adapted to penetrate at least one seal of the sample container.

In some embodiments, the sample container comprises an opening adapted for receiving the distal end of insertion tube of the endoscope.

In some embodiments, the sampling device is adapted for single use.

In some embodiments, a set of medical sampling parts or a sampling system for the use with an endoscope, said set of medical sampling parts or said sampling system comprising a sampling device according to the fifth aspect and a sampling container adapted for attachment to said sampling device.

In some preferred embodiments, a set of medical sampling parts or a sampling system for the use with an endoscope said set of medical sampling parts or said sampling system comprising: a sampling device device for the use with an endoscope having a suction channel and a suction connector in communication with said suction channel, said sampling device being adapted for connection to the suction connector and said sampling device being adapted for connection to a vacuum source, wherein said sampling device is adapted for forming a rigid connection with said endoscope when connected to the suction connector thereof; and a sampling container adapted for attachment to said sampling device, wherein the sampling device may comprise a sample container connector adapted for connecting a sample container. The sample container connector may extend in a direction parallel to or coincident with said insertion direction, wherein, apart from having a receptacle for receiving the connector, the sampling device may furthermore comprise a sample container connector comprising a pair of tubular protrusions adapted to engage and be inserted through the wall of a preferably detachable sample container, preferable through openings covered by a membrane, the tubular protrusions may preferably be arranged in such a manner on the sampling device that when the sampling device is correctly attached to the endoscope with the connector in the receptacle of the sampling device, the tubular protrusions extend in a direction transversely to the longitudinal direction of the endoscope, wherein the connector may extend itself transversely to the longitudinal direction of the endoscope, this means that the tubular protrusions of the sample container connector extend in parallel with the receptacle and consequently in parallel with the connector of the endoscope, i.e. in parallel with the insertion direction or possibly even coincident therewith.

This has the advantage that displacements, such as jerks when detaching or attaching the sample container will mainly be in the transverse direction to the endoscope and therefore be less likely to cause any displacement of the endoscope in the longitudinal direction, i.e. the aforementioned endoscope insertion direction. Such longitudinal displacement is undesired as the displacement could cause the tip of the endoscope to move within the patient, which could result in loss of the wedge position and thereby extend the time for the procedure.

In this disclosure, the term translational movement may be defined as denoting or relating to the movement of a body from one point of space to another and/or to the movement of every point of a body by the same distance in a given direction.

In this disclosure, a hydraulic diameter, $D_H$, is defined as follows $$D_H = 4A/P$$

Where A is the cross-sectional area of the flow, and P is the wetted perimeter of the cross-section. This allows a calculation of a corresponding diameter for non-circular pipe flows while ensuring that the hydraulic diameter of a flow in a circular pipe is the inner diameter of the pipe.

A person skilled in the art will appreciate that any one or more of the above aspects of the invention and embodiments thereof may be combined with any one or more of the other aspects of the invention and embodiments thereof.

BRIEF DESCRIPTION OF THE DRAWINGS

In the following, the invention will be described in more detail with reference to the drawings, in which:

FIG. 4A is another exploded perspective view of the set of medical sampling parts shown in FIG. 3A from a different angle;

FIG. 4B is the set of medical sampling parts shown in FIG. 4A in an assembled state;

FIG. 6A is a side view of the set of medical sampling parts in the assembled state;

FIG. 6B is a top view of the set of medical sampling parts in the assembled state showing section line A-A;

FIG. 8A is a perspective view of a sample container according to the second aspect of the invention;

FIG. 8B is a side view of the sample container of FIG. 8A showing section line C-C and detail view D;

DETAILED DESCRIPTION

Figure 1:
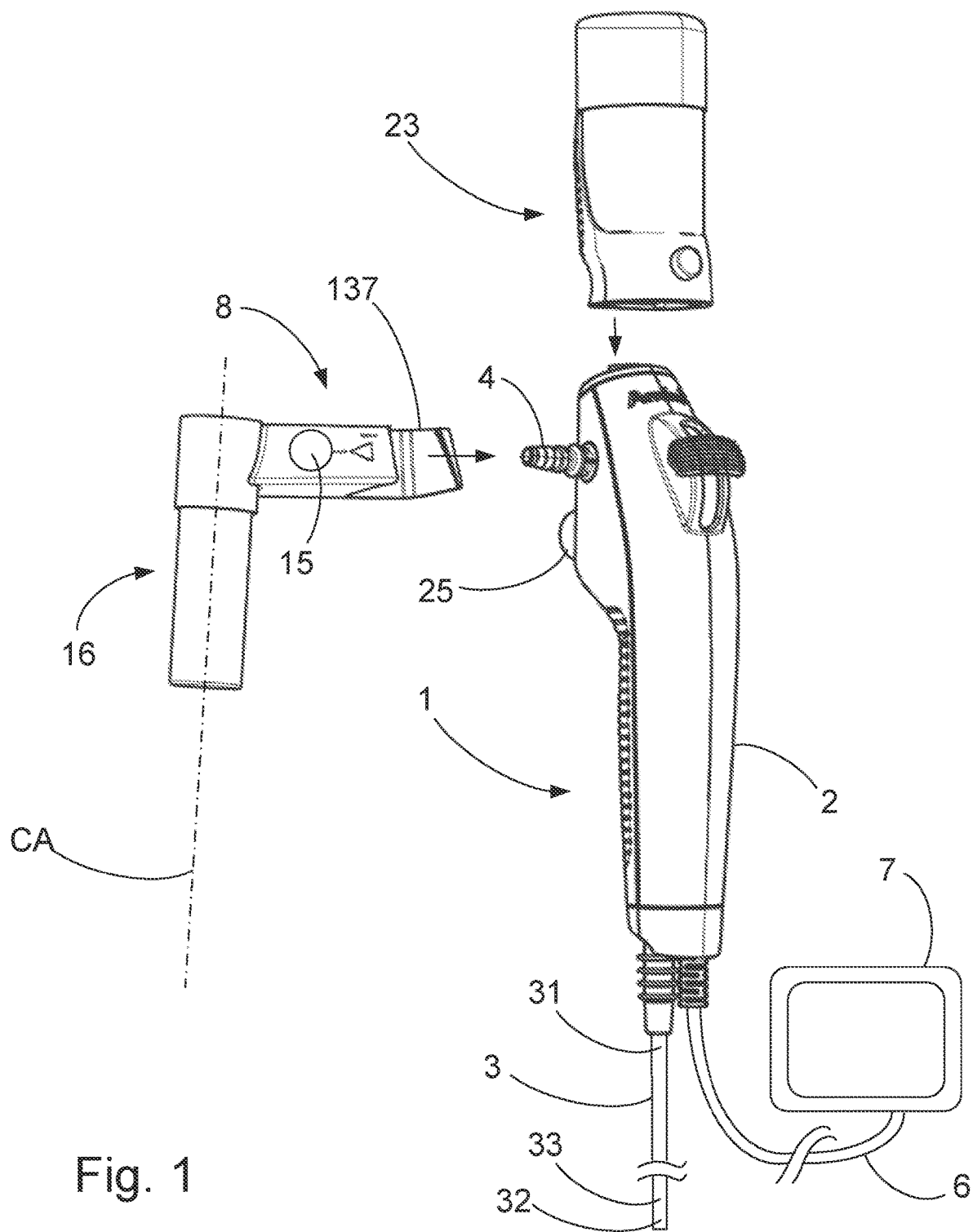
FIG. 1 is a perspective view of an endoscope connected to a schematically drawn monitor, a schematically drawn assembled set of medical sampling parts according to the first aspect of the invention and a saline cartridge both shown not connected to the endoscope.

Referring FIG. 1, an endoscope 1 is a medical device suitable for examination of natural and/or artificial body openings, e.g. for exploration of a lung cavity. The endoscope 1 comprises an operating handle 2, an elongated insertion tube 3, and a suction connector 4. For illustration purposes, the insertion tube 3 is only shown in part in FIG. 1. The endoscope 1, the sampling device 8, and the sample container 16 are adapted to and intended for single use. The sampling device 8 and the sample container 16 are shown detached from the endoscope 1, but may be attached to the endoscope 1 to bring the set of medical parts in an operating state. The sampling device 8 may be connected to a catheter instead of the endoscope 1. In FIG. 1, the sampling device 8 and the sample container 16 are schematically illustrated.

Figure 2A:
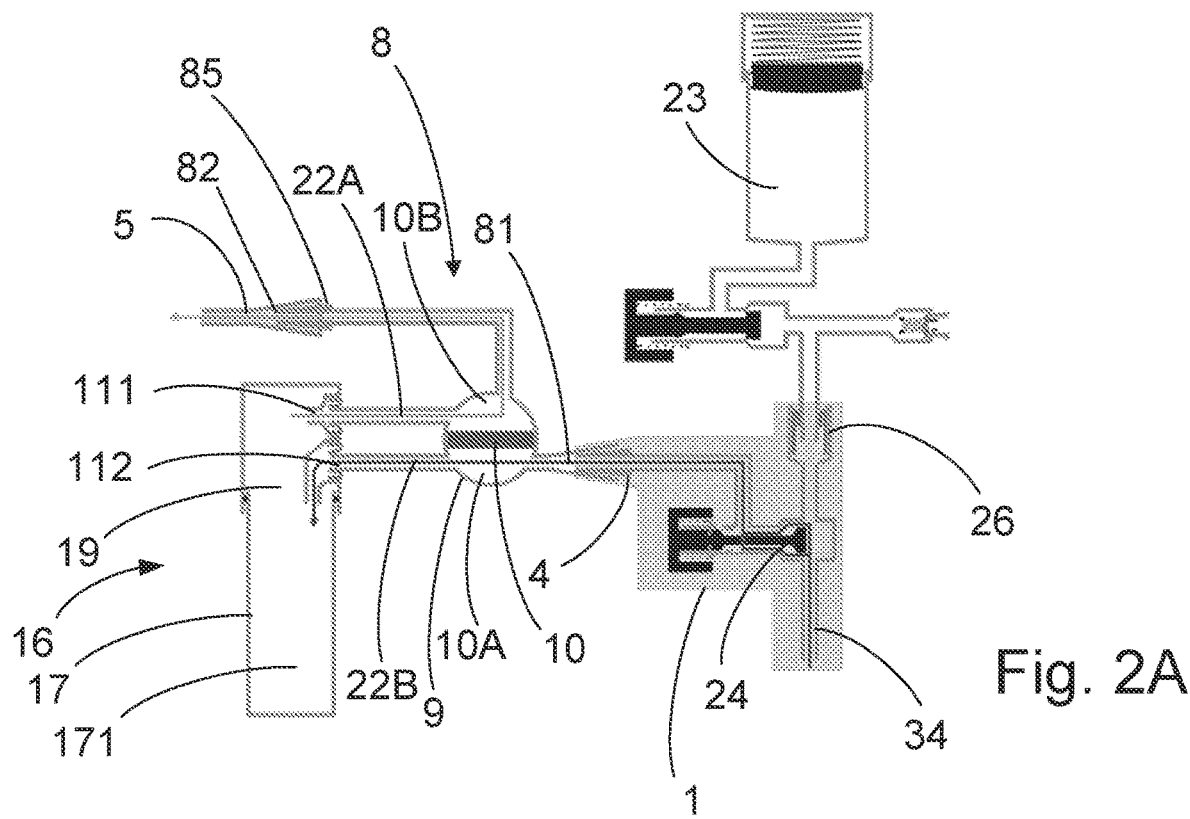
FIG. 2A is a schematic diagram of a set of medical sampling parts comprising the parts of FIG. 1 in an operating state and set to a first position of a sampling valve 9 of the sampling device 8.
Figure 2B:
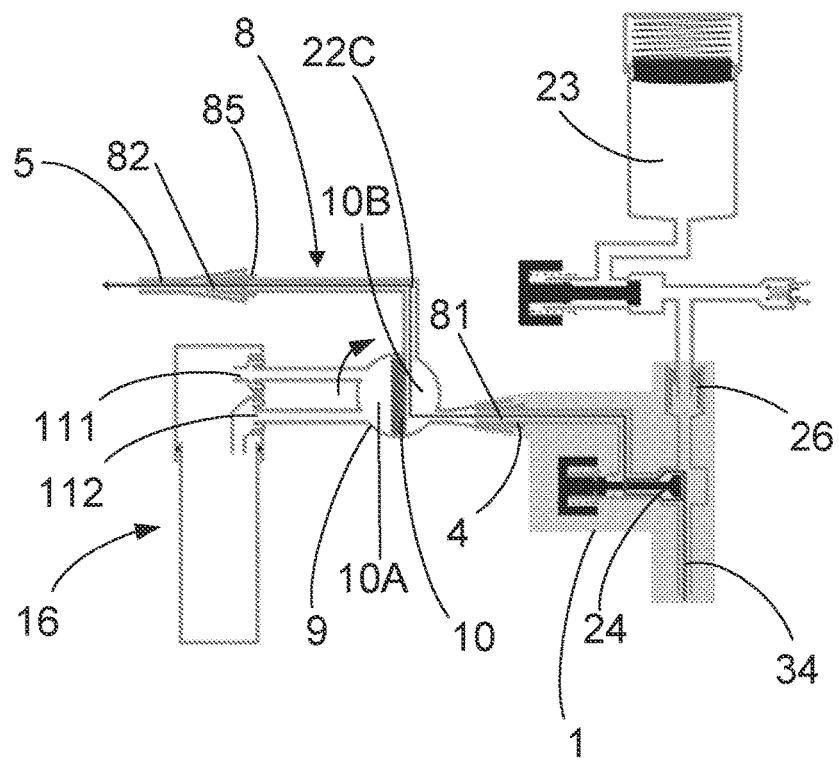
FIG. 2B is a schematic diagram of the set of medical sampling parts of FIG. 2 set to a second position of a sampling valve 9 of the sampling device.

FIGS. 2A and 2B are schematic diagrams of a set of medical sampling parts comprising the parts of FIG. 1 in an operating state and a sampling valve 9 of the sampling device 8 set to a sampling mode and a bypass mode, respectively. The sampling valve 9 has a valve member 10 that defines a first chamber 10A and a second chamber 10B. When the sampling valve 9 is in the sampling mode, the first chamber 10A fluidly connects the suction inlet 81 with a sampling inlet 112 (best seen in FIG. 4A) of a connector 11 to define a first fluid connection 22B and the second chamber 10B fluidly connects the suction outlet 82 with a sampling outlet 111 of the connector 11 to define a first fluid connection 22A, and sampling fluid is allowed to flow through the sample container 16 via the first and second fluid connections 22A, 22B, and, when the sampling valve 9 is in the bypass mode, sampling fluid is allowed to flow via a third, different, fluid connection 22C between the suction inlet 81 and suction outlet 82 of the sampling device 8, bypassing the connector 11. As seen on FIG. 2B, the sample container 16 is not a part of the third fluid connection 22C.

The endoscope 1 includes a suction channel 34 and a suction connector 4 in fluid connection with suction channel 34. In the shown operating state, the sample container 16, the sampling device 8, and the connector 11 are in the assembled state and the suction connector 4 is in fluid connection with the suction inlet 81 of the sampling device 8, so that the first fluid connection 22A extends through said suction channel 34 via the suction connector 4 of the endoscope 1 or catheter, so that flushing of a body cavity can be performed and/or a sample of bodily fluids and/or bodily tissue can be conveyed to the sample container 16. The operating handle has a bottom to which the proximal end 31 of the insertion tube 3 is connected. The sample container 16 is located at a greater height than the bottom of the operating handle 2 along the container axis CA, as best seen on FIG. 1, when the set of medical parts 1, 8, 11, 16 are in the operating state as seen on FIGS. 2A and 2B.

Referring to FIG. 1, the insertion tube 3 is an elongated member suitable for insertion into a patient, such as into a patient's lung through the patient's mouth. The insertion tube 3 extends from the operating handle 2 towards a distal end of the endoscope 1. The insertion tube 3 has a proximal end 31 connected to a handle housing of the handle 2 and a distal end 32 with a steerable, bendable tip part 33 allowing the insertion tube 3 to be maneuvered through the body cavities. Such body cavities may include trachea and bronchi of the patient, specifically in case of use of the medical system of FIG. 1 for bronchial or bronchoalveolar lavage, but, as will be appreciated by a person skilled in the art, the use of the medical sampling device according to the present invention is not necessarily limited to such procedures.

The distal tip of the tip part 33 comprises openings connected to one or more channels at least one of which, such as a suction channel, may be used as a suction channel 34, see also FIGS. 2A and 2B. The suction channel 34 may be connected to a suction or vacuum source via the suction connector 4 by the activation of a valve 9 operated by a push-button 25 on the handle 2 of the endoscope 1 in a well-known manner. The tip part 33 furthermore includes a light source and a camera connected via a cable 6 to the monitor 7, allowing the operator and others to monitor the actions performed within the patient.

The suction connector 4 is of a standard type for attaching a flexible suction tube, which is in turn to be connected to a vacuum or suction source, e.g. a wall suction as is often present in hospital rooms. The suction connector 4 is a generally tubular, frustoconically shaped male connector provided with a taper to allow easy connection of the flexible suction tube and with circumferential corrugations or barbs allowing a secure connection of the flexible suction tube in a well-known manner. The connector 4 need not be an integral part of the endoscope 1; in some alternative endoscopes, the connector is a separate, interchangeable part. Furthermore, in some alternative endoscopes, the connector may be a receptacle or a socket, i.e. a female connector.

FIG. 1 also shows the medical sampling device 8, which is an embodiment of the first aspect of the invention, and the saline cartridge 23, both adapted to be attached to the endoscope 1 by a movement in respective directions of the arrows in the figure, whereby the saline cartridge 23 is positioned into fluid communication with the working channel or suction channel 34 thereof.

In the set of medical sampling parts illustrated schematically in FIGS. 2A and 2B, rather than connecting a flexible suction tube directly to the suction connector 4, the sampling device 8 is connected to the suction connector 4. The sampling device 8, in turn, is then connected to a flexible suction tube 5. For this purpose, the sampling device 8 has an identical, similar or at least corresponding tube connector or suction connector 85, to which the flexible suction tube 5 may be attached, and an opening or receptacle constituting a suction inlet 81 acting as a socket for receiving and securing the suction connector 4. Evidently, if the connector 4 is a separate, interchangeable part as mentioned above, the sampling device 8 could be adapted to fit directly into the endoscope 1 so as to entirely avoid the suction connector.

The sampling device 8 further comprises a connector 11 (best seen in FIGS. 3A, 4A, 5, 7A and 7B) for connection to a sample container 16, the connector comprising a sampling inlet 112 and a sampling outlet 111 adapted to engage and be inserted through the wall of the preferably detachable sample container 16, preferably through openings covered by a membrane. Preferably, the sample container 16 is adapted to self-seal when the sample container 16 is detached from the sampling device 8.

The saline cartridge 23 is adapted to be attached to the endoscope 1 in fluid communication with the suction channel 34 thereof via an inlet port 26 of the endoscope 1. The saline cartridge 23 is a canister pre-filled with a saline solution and with a known pressurization device for exerting pressure on the saline solution.

Referring to FIGS. 3A, 3B, 4A, 4B, 5, 6A and 6B, a set of medical sampling parts 8, 11, 16 for use with an endoscope or catheter for flushing of a body cavity and/or for sampling of bodily fluids and/or bodily tissue, the endoscope or catheter having a suction channel and a suction connector in fluid connection with said suction channel, is provided. The set of medical sampling parts 8, 11, 16 comprises a sampling device 8, a sample container 16, and a connector 11 for connecting the sampling device 8 with the sample container 16.

The sampling device 8 includes a suction inlet 81 for connection to a suction connector of the endoscope or catheter, and a suction outlet 82 for connection to a vacuum source (not shown). The sampling device 8 is made of a rigid material, here a dimensionally stable polymer.

The sample container 16 includes: a cap part 18 comprising and accommodating a separator part 19 located at a top 161 of the sample container, a base 172 located at a bottom 162 of the sample container 16 opposite of said top 161, a container part 17 at least partly enclosing a sample volume 171 located at the bottom 162 of the sample container 16, and a container axis CA that extends between the separator part 19 and the base 172. The sample container 16 further comprises a side wall 174 connecting the top 161 and bottom 162 and extending in parallel with the container axis CA. The cap part 18 further comprise a container locking device 182 having a snap lever 183 configured to lock the sample container 16 to the sampling device 8 in the assembled state by snap locking as seen in FIG. 6A. The locking device is configured to be operated with a thumb of one hand when gripping the sample container 16 by having a thumb-sized operation area 184 as seen in FIG. 6B.

The base 172 allows stable support of the sample container 16 on a level surface, so that the container axis CA is substantially perpendicular to a surface level of a liquid sample (not shown) when a liquid sample is contained in the sample volume 171 and the base rests on a level support surface (not shown). The container axis CA extends between the oppositely located base 172 and cap part 18 of the sample container 16.

The connector 11 is an integral part of the sampling device 8 and is a protrusion in the form of a spout extending along the detachment axis DA. The connector comprises a flow path extension device. The connector comprises: a sampling inlet forming part of the first fluid connection and being able to eject sampling fluid into the sample container along an inlet direction; and a sampling outlet forming part of the second fluid connection and being able to discharge sampling gas of the sampling fluid along an outlet direction.

Referring to FIGS. 3B, 4B, 6A and 6B, the set of medical sampling parts 8, 11, 16 has an assembled state, in which the sampling device 8 and the sample container 16 are rigidly attached to each other by means of said connector 11 as shown in FIGS. 3B, 4B, 6A and 6B. The sample container 16 is radially fixed to the sampling device 8 in relation to the detachment axis DA by the connector 11 and longitudinally fixed to the sampling device 8 in relation to the detachment axis DA by a container locking device 182. An angle between a centre axis SIA of the suction inlet 81 and said container axis CA is fixed as measured in a plane defined by the centre axis SIA and the container axis CA as seen in FIG. 6A.

Figure 5:
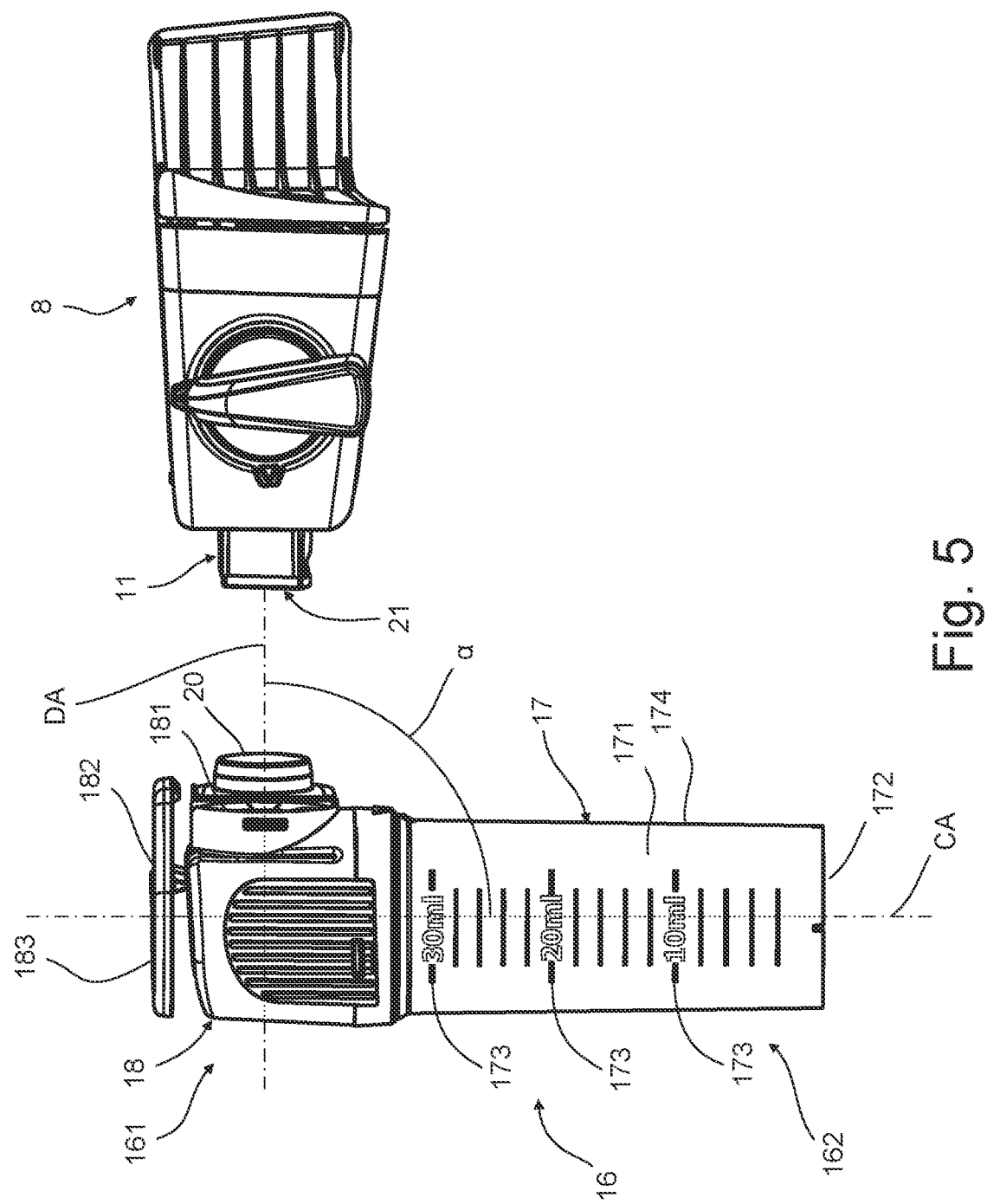
FIG. 5 is a side view of the set of medical sampling parts in the detached state.

The set of medical sampling parts 8, 11, 16 has a detached state, in which the sample container 16 is detached from the sampling device 8 as shown in FIG. 5.

As best seen in FIG. 2A, a first fluid connection 22A is established between the sample container 16 and the suction inlet 81, and a second fluid connection 22B is established between the sample container 16 and suction outlet 82, so that, when a sampling fluid (not shown) comprising liquid and gas enters the sample container 16 via the first fluid connection 22A, the sampling fluid can be separated in the separator part 19 of the sample container 16 by discharging liquid of the sampling fluid into said sample volume 171 and by discharging the gas of the sampling fluid via said second fluid connection 22B. The first and second fluid connections 22A, 22B are rigid connections in the assembled state.

Referring to FIGS. 5 and 6A, the sample container 16 can, when in the assembled state shown in FIG. 6A, be detached from the sampling device by a single translational movement of the sample container 16 along a detachment axis DA to bring the set of medical sampling parts to said detached state as seen in FIG. 5. The detachment axis DA intersects the container axis CA. A smallest angle α between said container axis CA and said detachment axis DA is equal substantially 90 degrees as best seen in FIG. 5. The smallest angle α is measured in a plane defined by the container axis CA and the detachment axis DA as the view in FIG. 5 represent. The container axis CA is vertical if the sample container rests on a level surface only supported by the base as best seen on FIG. 5. The container axis CA is a rotational symmetry axis of the cylindrical container part 17, alternatively the container part 17 may be box-shaped and, in this case, the container axis is a centre axis of the box shaped container part. The detachment axis DA extends through the side wall 174 in the assembled state.

Figures 3A, 3B:
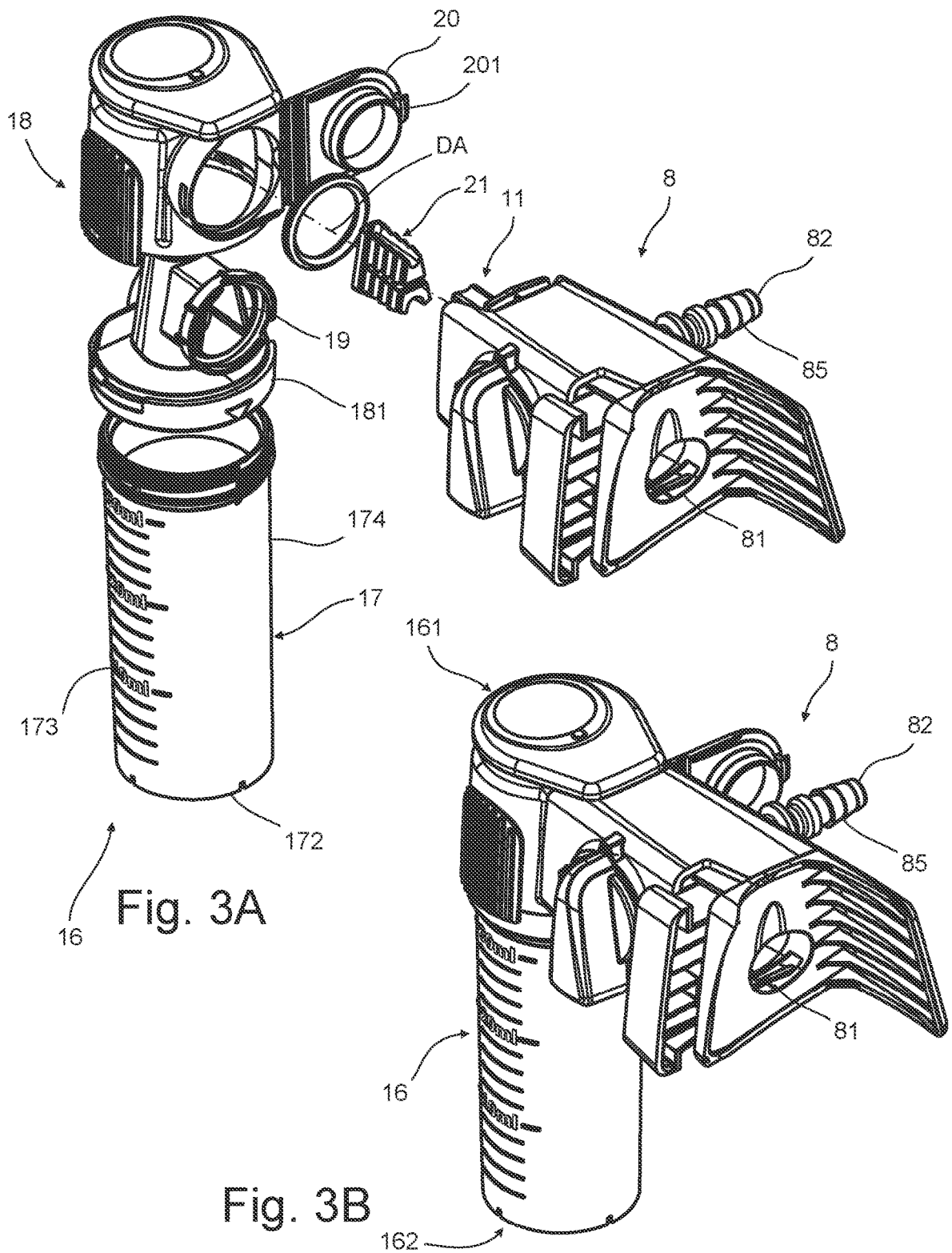
FIG. 3A is an exploded perspective view of the set of medical sampling parts showing the interconnections of the set of medical sampling parts.
FIG. 3B is the set of medical sampling parts shown in FIG. 3A in an assembled state.

The cap part 18 is removable from the remaining parts of the sample container 16 as best seen in FIGS. 3A and 4A and the container part 17 has the form of a hollow cylinder closed at one end, which is closed with the cap part 18 by screwing the cap part 18 onto the container part 17.

The sample container 16 can, when in the detached state shown in FIG. 5, be attached to the sampling device by a single translational movement of the sample container 16 along an attachment axis (not shown) coinciding with the detachment axis DA to bring the set of medical sampling parts to the assembled state as, for instance, seen in FIG. 6A.

Figure 7A:
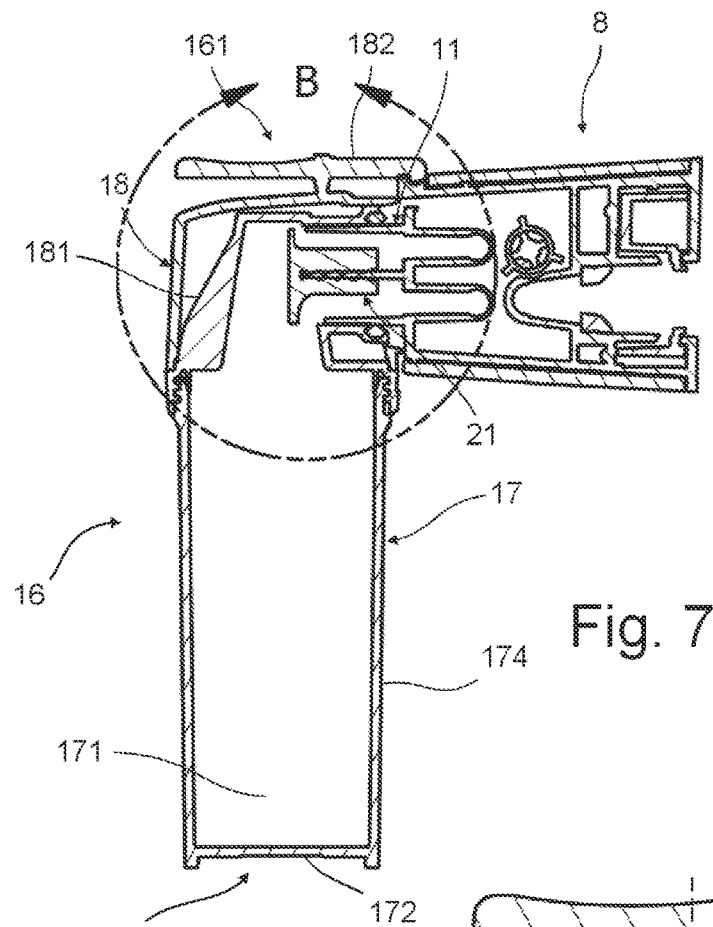
FIG. 7A is a cross-sectional view of the set of medical sampling parts along the A-A section line of FIG. 6B showing detail view B.
Figure 7B:
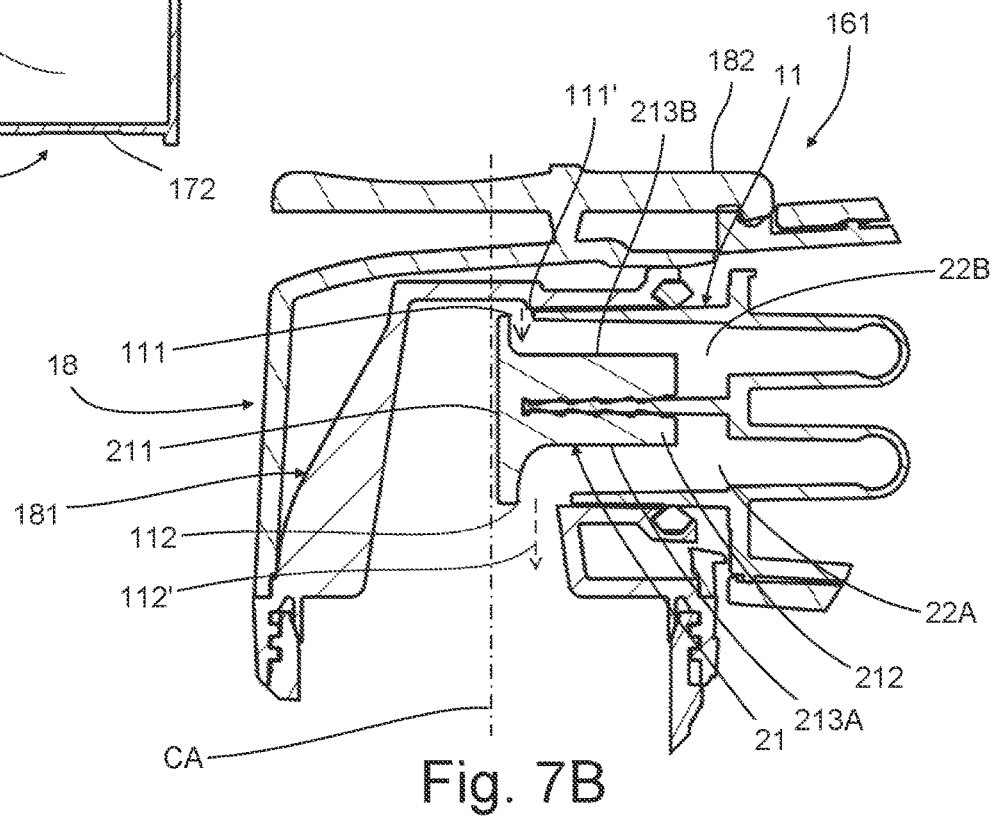
FIG. 7B is detail cross-sectional view B of the set of medical sampling parts of FIG. 7A.

Referring to FIGS. 7A and 7B, the flow path extension device 21 causes a centre flow path of gas of the sampling fluid flowing between the sampling inlet 112 and the sampling outlet 111 to be extended or prolonged compared to if the flow path extension device was not present. The flow path extension device 21 is a separate part. The flow path extension device 21 reduces a hydraulic diameter of a portion of the first fluid connection 22A, in particular the sampling inlet 112, and of the second fluid connection 22B, in particular the sampling outlet, relative to if the flow path extension device 21 is not present in the assembled state.

The flow path extension device 21 is in the form of an elongated plug extending along the detachment axis DA in the assembled state and comprising a head 211 and a body 212. The flow path extension device 21 has been inserted into the sampling inlet 112 and the sampling outlet 111 of the connector 11 in the assembled state. The body comprises a first duct 213A and a second duct 213B, wherein the first duct 213A forms a first part of the first fluid connection 22A in the assembled state, and the second duct 213B forms a second part of said second fluid connection 22B in the assembled state, so as to reduce the hydraulic diameter of the sampling inlet 112 and the sampling outlet 111 compared to if the flow path extension device 21 was not present. The flow path extension device 21 is made of a rubber material, so that the flow path extension device 21 seals the connector 11, so as to urge the sampling fluid to enter the sample container 16 along an inlet direction 112' of the sampling inlet 112, and to leave the sample container 16 along an outlet direction 112' of the sampling outlet 111. The body 212 of the flow path extension device 21 comprise a barb 214 adapted for resisting removal of the flow path extension device 21 from the connector 11.

The angle between the inlet direction 112' and the container axis CA is fixed. The sampling outlet 111 is located closer to the top 161 of the sample container 16 relative to the sampling inlet 112 in the assembled state. The inlet direction 112' and outlet direction 111' extend in parallel with the container axis. The sampling inlet 112 has a first hydraulic diameter and the sampling outlet has a second hydraulic diameter, the first hydraulic diameter is approximately 2 times greater than the second hydraulic diameter.

The container part 17 further comprises three major liquid level marks allowing visual measurement of the volume of liquid (not shown) contained in the sample volume 171 of the container part 17. The liquid level marks extend in a plane perpendicular to the container axis CA. The liquid level marks are adapted to extend in parallel to a liquid level of a liquid sample (not shown) in the sample volume 171 of the sample container 16 when the base 172 rests on a level surface.

FIGS. 8A and 8B show a sample container 16 for connecting to a connector 11 of a sampling device 8, comprising: a container part 17, a cap part 18, a base 172, and a container axis CA. The container part 17 at least partly encloses a sample volume 171 located at a bottom 162 of the sample container 16. The cap part 18 is located at a top 161 of the sample container 16 and includes an insertion hole 181, which can receive and attach the connector 11 and can establish a fluid connection between the sampling device 8 and the sample volume 171 of the container part 17. The insertion hole 181 extends along a detachment axis DA. The base 172 is for supporting the sample container 16, and is located oppositely from the cap part 18 at the bottom 162 of the sample container 16. The container axis CA extends between the cap part 18 and the base 172 of the sample container 16. The cap part 18 and the container part 17 can be detached from each other by screwing. The distance between the inlet of the insertion hole 19 into the sample container 16 and the bottom of the sample volume 171 is approximately 75 mm along the container axis CA.

Figure 9A:
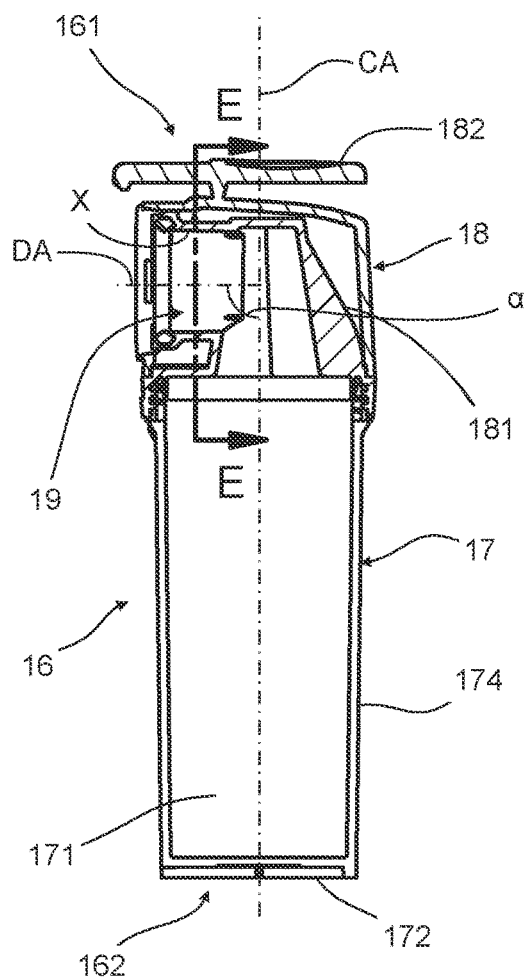
FIG. 9A is a cross-sectional view of the sample container along the section line C-C of FIG. 8B showing section line E-E.
Figure 9B:
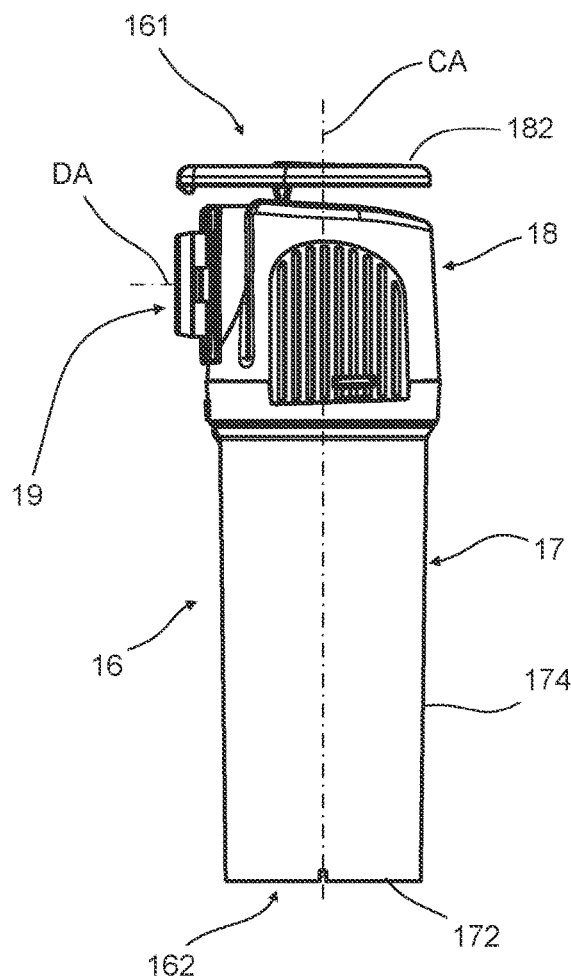
FIG. 9B is a side view of the sample container of FIG. 8A.

Referring to FIG. 9A, a smallest angle α between said container axis and the detachment axis is approximately 90 degrees. The insertion hole 181 has a cross-sectional shape 191, which is perpendicular to said detachment axis DA, and which extends substantially uniformly for approximately 9 mm in length.

Figure 10A:
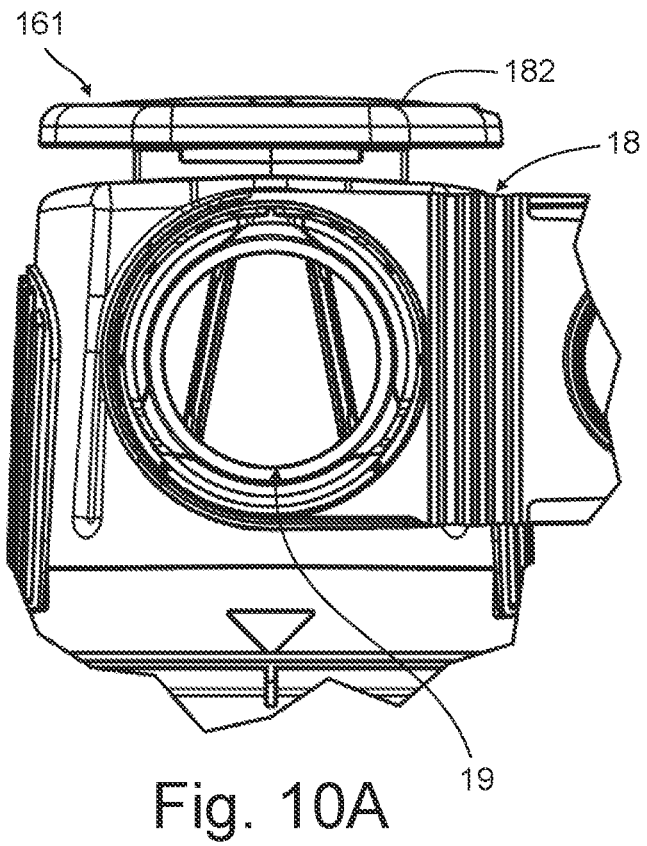
FIG. 10A is a detail view D of the sample container of FIG. 8B.
Figure 10B:
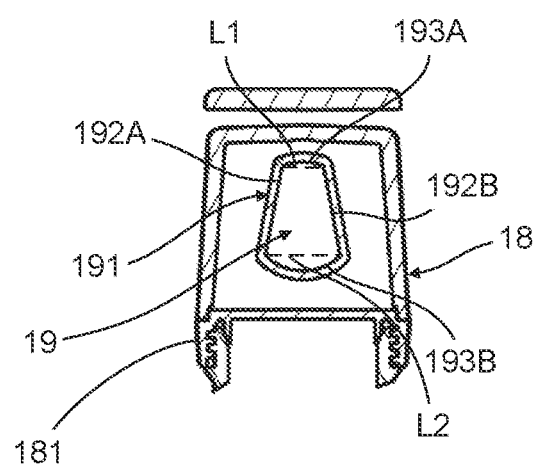
FIG. 10B is a cross-sectional view of the sample container along section line E-E of FIG. 9A.

Referring to FIG. 10B, the cross-sectional shape 191 is a substantially convex keyhole shape, so that when said connector 11 is inserted into the insertion hole 19 along said detachment axis DA, if the connector 11 has an exterior shape corresponding to the cross-sectional shape 191 of the insertion hole 19, said connector 11 can be at least radially fixed, in said insertion hole 19 in relation to said detachment axis DA, and the sample container 16 can be attached and detached from the sampling device 8 by a translational movement of the sample container 16 along said detachment axis DA. The cross-sectional shape 191 is convexly keyhole shaped so that attaching the sample container to the sampling device can only happen with one orientation of the sample container 16. The cross-sectional shape 191 of the insertion hole 19 may be a quadrilateral with a first pair of opposite sides 192A, 192B having equal length and a second, different pair of opposite sides 193A, 193B having unequal length. The first pair of sides 192A, 192B is reflection symmetrical in a plane defined by the detachment axis DA and the container axis CA. The length of each side of the first pair of sides 192A, 192B of the quadrilateral is between 11.6-12.2 mm. The distance between the end points of the top side of the second pair of sides, L1, is approximately 53% of the distance between the end points of the bottom side of the second pair of sides, L2. The distance between the end points of the top side of the second pair of sides, L1, is between 4.6-5.2 mm, and the distance between the end points of the bottom side of the second pair of sides, L2, is between 8.9-9.5 mm.

Both sides of the second pair of sides 193A, 193B of the quadrilateral are convexly or outwardly curved, and have equal curvature, and have a common centre of curvature. The curvature of each of the second pair of sides 193A, 193B of the quadrilateral has a diameter, D, between 14.0-14.7 mm.

The sample container 16 further comprises a container locking device 182 adapted to lock the sample container 16 to a sampling device 8 upon connection. The container locking device 182 comprises a snap lever 183 which snaps around a ridge of the sampling device 8 upon connection thereto. The container locking device 182 further comprises an operation surface 184 allowing a user to disengage, and engage, the locking device with one hand.

The sample container 16 further comprises a sealing lid 20 having a closed state (not shown), in which the sealing lid 20 sealingly close the insertion hole 19, and an open state, which is shown in FIGS. 8A and 8B. The sealing lid 20 is hingedly connected to the cap part 18 of the sample container 16. The sealing lid 20 allow a user to close the sealing lid with one hand by gripping the container part 17 with the palm of a hand and close the lid with a thumb of the same hand by rotating the sealing lid 20 around its hinged connection to the cap part 18. The sealing lid 20 further comprises a lid locking device 201 able to lock the sealing lid 20 in the closed state by snap locking it to the cap part 18.

The following is a list of reference numerals used throughout this specification.

1 endoscope
2 operating handle
24 endoscope valve
25 push button
26 inlet port
3 insertion tube
31 proximal end
32 distal end
33 steerable tip part
34 suction channel
4 suction connector
5 suction tube
6 cable
7 monitor
8 sampling device
81 suction inlet
82 suction outlet
85 suction connector
9 sampling valve
91 first suction channel
92 first sampling channel
93 second suction channel
94 second sampling channel
95 first valve port
96 second valve port
97 third valve port
98 fourth valve port
10 valve member
10A first chamber
10B second chamber
11 connector
111 sampling outlet
111' outlet direction
112 sampling inlet
112' inlet direction
16 sample container
161 top
162 bottom
17 container part
171 sample volume
172 base
173 liquid level mark
174 side wall
18 cap part
181 separator part
182 container locking device
183 snap lever
184 operation surface
19 insertion hole
191 cross-sectional shape
192A, 192B first pair of sides
193A, 193B second pair of sides
20 sealing lid
201 lid locking device
21 flow path extension device
211 head
212 body
213A, 213B duct
214 barb
22A first fluid connection
22B second fluid connection
22C third fluid connection
CA container axis
DA detachment axis
α smallest angle
23 saline cartridge

We claim:

1. A set of medical sampling parts comprising:
a sample container including a cap part, a top, and a container part detachably attached to the cap part,
the container part having a container axis,
and the cap part including a snap lever and an insertion hole disposed between the snap lever and the container part,
the sample container configured to receive a sampling fluid from a medical device
and a sampling device connecting the medical device to the top of the sample container and defining a detachment axis along a length of the sampling device,
the sampling device made of or comprising a rigid material to establish a rigid connection between the sample container and the medical device,
the sampling device comprising a locking ridge,
a sampling inlet and a sampling outlet, the sampling inlet and the sampling outlet penetrating through the insertion hole of the cap part in an assembled state of the set of medical sampling parts, wherein the snap lever engages the locking ridge to removably secure the sample container to the sampling device in the assembled state of the set of medical sampling parts wherein the sampling device comprises a suction inlet and a suction outlet, wherein when attached to the sampling device the medical sampling parts establish a first fluid connection between the suction inlet and the sample container and a second fluid connection between the sample container and the suction outlet, so that, when the sampling fluid, comprising liquid and gas, enters the sample container via the first fluid connection, the sampling fluid can be separated by discharging the gas of the sampling fluid via the second fluid connection;

and wherein the sampling outlet is located closer to the top of the sample container relative to the sampling inlet in the assembled state.

2. The set of medical sampling parts of claim 1, wherein the sampling inlet has a first hydraulic diameter and the sampling outlet has a second hydraulic diameter smaller than the first hydraulic diameter.

3. The set of medical sampling parts of claim 1, wherein the snap lever is cantilevered.

4. The set of medical sampling parts of claim 1, wherein an angle between the detachment axis and the container axis is at least 45 degrees.

5. The set of medical sampling parts of claim 1, further comprising a connector having a sampling inlet and a sampling outlet parallel to the sampling inlet and extending along the detachment axis.

6. The set of medical sampling parts of claim 5, wherein the sampling device comprises the connector.

7. The set of medical sampling parts of claim 5, wherein the cap part includes an insertion hole configured to receive and attach the connector.

8. The set of medical sampling parts of claim 7, wherein the cap part includes an insertion hole configured to receive and attach the connector, and wherein the insertion hole and the connector have cross-sectional keyhole shapes.

9. The set of medical sampling parts of claim 1, wherein the sampling device further comprises a sampling valve having a bypass mode and a sampling mode, wherein, when the sampling valve is in the sampling mode, sampling fluid is allowed to flow through the sample container via the first fluid connection and the second fluid connection, and wherein, when the sampling valve is in the bypass mode, the sampling fluid is allowed to flow via a third, different, fluid connection between the suction inlet and the suction outlet of the sampling device.

10. The set of medical sampling parts of claim 9, further comprising the medical device, wherein the medical device comprises a suction channel and a suction connector, wherein when assembled with the sampling device the suction connector is in fluid connection with the suction inlet of the sampling device, and wherein the first fluid connection extends through the suction channel via the suction connector so that flushing of a body cavity can be performed and/or a sample of bodily fluids and/or bodily tissue can be conveyed to the sample container.

11. The set of medical sampling parts of claim 10, wherein the medical device comprises an endoscope or a catheter.

12. The set of medical sampling parts of claim 10, wherein medical device comprises an endoscope, wherein the endoscope comprises a handle having a proximal end opposite a distal end and an insertion tube extending from the distal end of the handle, wherein at least the top of the sample container is located, along a longitudinal axis of the handle, closer to the proximal end than the distal end of the handle.

13. The set of medical sampling parts of claim 1, further comprising a flow path extension device, wherein a centre flow path of gas of the sampling fluid flowing between the sampling inlet and the sampling outlet is extended or prolonged compared to if the flow path extension device was not present.

14. The set of medical sampling parts of claim 13, wherein a hydraulic diameter of a portion of the first fluid connection and/or of the second fluid connection is reduced compared to if the flow path extension device was not present.

15. The set of medical sampling parts of claim 13, further comprising a connector, wherein the flow path extension device is in the form of a plug comprising a head and a body, the flow path extension device being inserted into the connector in an assembled state of the medical sampling parts.

16. The set of medical sampling parts of claim 15, wherein the body comprises a duct forming part of the first or the second fluid connection in said assembled state, so as to reduce the hydraulic diameter of at least a portion of the first fluid connection and/or the second fluid connection compared to if the flow path extension device was not present.

17. A set of medical sampling parts comprising:

a medical device a sample container including a cap part and a container part detachably attached to the cap part, the container part having a container axis, and the cap part including a snap lever and an insertion hole disposed between the snap lever and the container part, the sample container configured to receive a sampling fluid from the medical device a sampling device connecting the medical device to the sample container and defining a detachment axis along a length of the sampling device, the sampling device made of or comprising a rigid material to establish a rigid connection between the sample container and the medical device, the sampling device comprising a locking ridge, a sampling inlet and a sampling outlet, the sampling inlet and the sampling outlet penetrating through the insertion hole of the cap part in an assembled state of the set of medical sampling parts, wherein the snap lever engages the locking ridge to removably secure the sample container to the sampling device in the assembled state of the set of medical sampling parts;

wherein the sampling device comprises a suction inlet and a suction outlet, wherein when attached to the sampling device the medical sampling parts establish a first fluid connection between the suction inlet and the sampling container and a second fluid connection between the sample container and the suction outlet, so that, when a sampling fluid comprising liquid and gas enters the sample container via the first fluid connection, the sampling fluid can be separated by discharging the gas of the sampling fluid via the second fluid connection, the set of sampling parts further comprising a flow path extension device, wherein a center flow path of gas of the sampling fluid flowing between the sampling inlet and the sampling outlet is extended or prolonged compared to if the flow path extension device was not present;

further comprising a connector, wherein the flow path extension device is in the form of a plug comprising a head and a body, the flow path extension device being inserted into the connector in an assembled state of the medical sampling parts.

18. The set of medical sampling parts of claim 17, wherein the medical device comprises an endoscope or a catheter.

* * * * *